United States Patent [19]

Leister et al.

[11] 4,246,180

[45] Jan. 20, 1981

[54] PROCESS FOR SEPARATING OFF 1-AMINO-4-BROMOANTHRAQUINONE-2-SULPHONIC ACID

[75] Inventors: Heinrich Leister; Helmut Dittmer, both of Leverkusen; Hubert Schönhagen, Odenthal, all of Fed. Rep. of Germany

[73] Assignee: Bayer Aktiengesellschaft, Leverkusen, Fed. Rep. of Germany

[21] Appl. No.: 938,724

[22] Filed: Aug. 31, 1978

[30] Foreign Application Priority Data

Sep. 10, 1977 [DE] Fed. Rep. of Germany ....... 2740888

[51] Int. Cl.³ ........................................ C07C 143/665
[52] U.S. Cl. .................................................. 260/371
[58] Field of Search ........................................ 260/371

[56] References Cited

U.S. PATENT DOCUMENTS 2,413,790 1/1947 Seymour et al. ..................... 260/371

OTHER PUBLICATIONS

*Chemical Abstract* vol. 82 #31183; "1-Amino-4-bromoanthraquinone" Nakahara 7/24/74.
*Chemical Abstract* vol. 78 No. 1-3 #15915m "Purification of 1-amino-4-bromo-2-anthraquinone sulfonic acid" Thuering 9/21/72.
*Chemical Abstract* vol. 69 No. 22-24 #96343n "1-Amino-4-haloanthraquinone 2-sulfonic acid dye intermediates" Hruska 3/15/67.

*Primary Examiner*—Patrick Garvin
*Assistant Examiner*—Raymond K. Covington
*Attorney, Agent, or Firm*—Sprung, Felfe, Horn, Lynch & Kramer

[57] ABSTRACT

A process for separating off 1-amino-4-bromoanthraquinone-2-sulphonic acid from the reaction mixture formed by the bromination of 1-aminoanthraquinone-2-sulphonic acid in sulphuric acid, which process comprises adjusting the sulphuric acid concentration of the reaction mixture under the prevailing conditions of temperature and pressure to effect precipitation of 1-amino-4-bromoanthraquinone-2-sulphonic acid as the sulphate and thereafter separating the resultant sulphate precipitate from the reaction mixture.

8 Claims, No Drawings

PROCESS FOR SEPARATING OFF 1-AMINO-4-BROMOANTHRAQUINONE-2-SULPHONIC ACID

BACKGROUND OF THE INVENTION

1. Field of the Invention

The invention relates to a process for separating off 1-amino-4-bromoanthraquinone-2-sulphonic acid, or the akali metal salts thereof, from reaction mixtures obtained from the bromination of 1-aminoanthraquinone-2-sulphonic acid in sulphuric acid.

2. Discussion of Prior Art

1-Amino-4-bromanthraquinone-2-sulphonic acid (termed bromamine-acid in the text which follows) is an important intermediate product for anthraquinone dyestuffs (compare Ullmans Encyklopädie der technischem Chemie (Ullman's Encyclopedia of Industrial Chemistry), 4th edition, volume 7, pages 639–640). It is prepared by sulphonating 1-aminoanthraquinone with sulphur trioxide or chlorosulphonic acid in sulphuric acid or in the presence of inert organic solvents (German patent specification Nos. 263,395 and 484,997, U.S. Pat. No. 3,428,659 and Japanese Published Specification No. 49,076,848) and brominating the resulting 1-aminoanthraquinone-2-sulphonic acid in an aqueous or aqueous-organic medium or in sulphuric acid (FIAT 1,313 II, page 214, U.S. Pat. Nos. 2,413,790 and 3,428,659 and Japanese Published Specification No. 49,076,848).

In the case of bromination in sulphuric acid in accordance with the Japanese Published Specification, the reaction mixture is worked up by dilution with a large excess of water. The bromamine-acid is precipitated in the form of its alkali metal salt by adding an alkali metal hydroxide solution and this salt is then isolated by filtration.

This working up has the disadvantage that filtrates with a high salt load are obtained, which represent a considerable load on the effluent. Processing of effluents having a high salt load is possible, for example by evaporation. However, this process not only involves a great deal of technical effort but large amounts of a residue of salt contaminated by organic substances are also formed. Thus, for example, when Example 1 of Japanese Pubished Specification No. 49,076,848 is repeated, about 7 kg of sodium sulphate or sodium bisulphate, per kg of bromamine-acid, are obtained as a result of neutralizing the sulphuric acid with sodium hydroxide solution.

A further disadvantage of working up by dilution with a large excess of water is that not only the bromamine-acid but also by-products of the sulphonation and the bromination, such as, for example, other sulphonic acids and 1-amino-2- and -4-bromo-anthraquinone and also, in particular, 1-amino-2,4-dibromoanthraquinone, are precipitated. These impurities are troublesome in most reactions of bromamine-acid to give dyestuffs and must therefore be removed previously.

According to the information in Japanese Published Specification No. 49,076,848, it is possible to remove the constituents which have not been sulphonated, such as 1-amino-2,4-dibromoanthraquinone, by shaking thoroughly with o-dichlorobenzene and separating off the organic phase. With this method, not only does the phase separation constitute a process step which is problematical from the technical point of view but it is also necessary, in order to keep the waste water pure, to free the aqueous phase from the proportions of organic solvents, which are always present, by distillation.

A further possibility for removing impurities is filtration to clarify the solution (compare, for example, Houben-Weyl, Methoden der organischen Chemie (Methods of organic Chemistry), 4th edition, volume I/1, page 185 et seq). For this purpose, the bromamine-acid precipitated from the reaction mixture is dissolved in hot water, active charcoal and/or a filter aid is added, the mixture is filtered and the bromamine-acid is again precipitated from the filtrate with the aid of alkali metal salts. Frequently, the required quality is obtained only by clarifying twice, for example in a weakly acid or weakly alkaline medium. The clarification process thus involves a considerable expenditure of time and on technical equipment and considerable costs. Moreover, large volumes of effluents which have to be processed are formed.

Broadly, this invention contemplates a process for separating off 1-amino-4-bromoanthraquinone-2-sulphonic acid from a reaction mixture formed during the preparation thereof by bromination of 1-aminoanthraquinone-2-sulphonic acid in sulphuric acid, which process comprises adjusting the sulphuric acid concentration of the reaction mixture under the prevailing conditions of temperature and pressure to effect precipitation of 1-amino-4-bromoanthraquinone sulphonic acid as the sulphate and thereafter separating the sulphate precipitate from the reaction mixture.

SUMMARY OF THE INVENTION

It has now been found that 1-amino-4-bromoanthraquinone-2-sulphonic acid, or alkali metal salts thereof, can be isolated in good purity and in a manner which is simple from the point of view of effluent technology, from the reaction mixture formed during its preparation by bromination of 1-amino-anthraquinone-2-sulphonic acid in sulphuric acid, when the concentration of sulphuric acid is adjusted, by mixing the reaction mixture with water, which optionally contains sulphuric acid, to a concentration that the 1-amino-4-bromoanthraquinone-2-sulphonic acid precipitates as the sulphate and the latter is isolated and converted into 1-amino-4-bromoanthraquinone-2-sulphonic acid, or the alkali metal salts thereof, by the action of water, if appropriate in the presence of alkali metal hydroxides, alkali metal oxides or alkali metal salts.

The reaction mixture from which the bromamine-acid is isolated can have been formed in any desired manner by bromination of 1-aminoanthraquinone-2-sulphonic acid in sulphuric acid, for example by bromination in aqueous, anhydrous or $SO_3$-containing sulphuric acid. It is also possible to use the reaction mixture which is obtained starting from 1-aminoanthraquinone by sulphonation with sulphur trioxide or chlorosulphonic acid and subsequent bromination in a one-pot process. Finally, the reaction mixture which forms according to Japanese Published Specification No. 49,076,848 can be employed. Inorganic salts, such as sodium sulphate, or catalysts, such as iodine, do not interfere.

The sulphuric acid concentration can be adjusted to the desired value in any desired manner, for example by stirring the reaction mixture into the water, which optionally contains sulphuric acid, or vice versa. A sulphuric acid concentration of about 60 to about 85% by weight, preferably about 65 to about 80% by weight, is obtained by this means.

The precipitation can be effected with or without external cooling. It has proved suitable to carry out the precipitation at temperatures in the range of about 50° to about 90° C., preferably 50° to 60° C. Temperatures higher than 90° C., for example up to about 120° C., are sometimes advantageous in order to obtain a better crystal form.

The adjustment of the sulphuric acid concentration is dependent upon the conditions of temperature and pressure in that the solubility product constant at the prevailing conditions of temperature and pressure must be exceeded to effect precipitation of the 1-amino-4-bromoanthraquinone-2-sulphonic acid as the sulphate. Thus, at a given pressure (usually atmospheric pressure) the temperature and required concentration of sulphuric acid are more or less directly proportional.

After filtering, th filter cake can be rinsed with dilute sulphuric acid in order to remove adhering mother liquor and the concentration of this acid should be between about 60% by weight and the concentration used for precipitation.

The bromamine-acid can be liberated from the sulphate, which has been isolated, by the action of water. For this purpose, the material on the filter can be washed until neutral with water to which a small amount of an alkali metal salt, such as sodium chloride, potassium chloride and/or sodium sulphate, has been added. However, for practical industrial use it is more advantageous to stir the filter cake with water, optionally with the addition of an alkali metal salt, such as, for example, sodium chloride, potassium chloride and/or sodium sulphate, or of alcaline substances, such as, for example, sodium hydroxide solution and or potassium hydroxide solution and/or sodium carbonate. In this case, the mixture should be stirred well and if necessary subjected to further heating, for example to about 90° C. The product is then filtered off, washed with dilute salt solution and dried.

The bromamine-acid, or the alkali metal salt thereof, isolated in this way are of good quality (about 93–95% pure, based on the free acid and waterfree material). Especially in the case of the preparation of bromamine-acid from 1-aminoanthraquinone by sulphonation and bromination in the one-pot process (compare Example 1,3,5 and 6,7,8,9), the yield and quality are far better when the product is isolated by the present process than when the reaction mixture is stirred into a large amount of water and subsequently clarified (compare Example 2).

A particular advantage of the process according to the invention is that the approximately 60% strength by weight to 80% strength by weight sulphuric acid obtained from the filtration of the bromamine-acid sulphate can be reconcentrated by known processes (compare, for example, Ullmans Encyklopädie der technischen Chemie (Ullman's Encyclopedia of industrial Chemistry), 3rd edition, volume 15, page 442 et seq.).

A further advantage is that the dilute sulphuric acid obtained when the suction filter cake containing sulphuric acid is stirred with water can be re-used as a mixing component. The load on the effluent is further reduced as a result of this recycling. Overall, about 80% of the sulphuric acid employed are recovered by reconcentrating and recycling.

In the temperature range and concentration range according to the process, bromamine-acid sulphate is surprisingly stable. Even if the temperature rises to 110°–120° C. (compare Example 1) when the reaction mixture is diluted with water, which optionally contains sulphuric acid, the product is not changed chemically. This was not to be foreseen since it is known from German patent specification Nos. 263,395 and 266,563 that bromamine-acid in 60% strength and 78% strength sulphuric acid already loses the sulphonic acid group at temperatures of about 150° C., it additionally being possible for the bromine atom to be shifted from the 4-position to the 2-position.

In the examples which follow, the percentages denote percentages by weight. The examples serve to illustrate the process according to the invention without, however, restricting it to these examples.

EXAMPLE 1

150 g of 96% pure 1-aminoanthraquinone are introduced into a mixture of 200 ml of 20% strength oleum and 100 g of anhydrous sodium sulphate, while stirring, and the mixture is heated to 130° C. in the course of 1 hour. This temperature is maintained for 2 hours, 120 ml of 20% strength oleum and 50 g of anhydrous sodium sulphate are added and the mixture is stirred for a further 3 hours at 130° C. The sulphonation has then virtually ended. For bromination, the mixture is cooled to 80° C., 0.2 g of iodine and about 0.5 ml of an antifoaming agent are added and 21 ml of bromine are allowed to run in in portions, at 80° C., in the course of 9 hours. The content of 1-aminoanthraquinone-2-sulphonic acid in a sample which has been worked up is then less than 1%.

For working up, excess bromine is first removed by briefly applying a vacuum and 140 ml of water are then allowed to run in dropwise in the course of 1 hour, during which time the temperature rises from 80° C. to 110° C. The bromamine-acid sulphate is filtered off at 50°–60° C. and rinsed with 300 ml of 60% strength sulphuric acid. The mother liquor and the washing liquor are combined and give 855 g of a 65% strength sulphuric acid, which can be reconcentrated by known processes.

The suction filter cake (668 g) is stirred in 1,800 ml of water, the pH value is adjusted to 8 by adding 308 ml of 50% strength sodium hydroxide solution and the mixture is heated at 90° C. for 1 hour. The mixture is then cooled to 60° C. and the sodium salt of bromamine-acid is filtered off, washed with 1,200 ml of a 1.5% strength sodium sulphate solution and dried. This gives 234.6 g having the following analysis:

87.5% of bromamine-acid
0.5% of 1-aminoanthraquinone-2-sulphonic acid
0.4% of constituents which have not been sulphonated
7.1% of water The yield of bromamine-acid is accordingly 83.2% of theory, based on 1-aminoanthraquinone.

EXAMPLE 2 (COMPARISON EXAMPLE)

Sulphonation and bromination were performed in accordance with Example 1, working up by stirring into a large excess of water and clarifying.

The reaction mixture obtained according to the instructions of Example 1 is stirred into 1,400 ml of water and filtered, the suction filter cake is stirred in 2,000 ml of water and the pH is adjusted to 8–9 by adding about 100 ml of 50% strength sodium hydroxide solution. For clarification, the mixture is heated to 95°–100° C., a mixture of 12 g of active charcoal and 12 g of kieselguhr is added, the resulting mixture is filtered through a pre-heated suction filter and the material on the filter is rinsed with 400 ml of hot water. The sodium salt of bromamine-acid is salted out with 36 g of sodium sulphate, filtered off at about 50° C., washed with 1,600 ml of 1.5% strength sodium sulphate solution and dried. This gives 187.2 g having the following analysis:
  88.2% of bromamine-acid
  0.5% of 1-aminoanthraquinone-2-sulphonic acid
  2.0% of constituents which have not been sulphonated
  4.7% of water The yield of bromamine-acid is accordingly only 66.9% of theory, based on 1-aminoanthraquinone.

EXAMPLE 3

220 ml of 60% strength sulphuric acid are allowed to run dropwise, to 50°–60° C., into the reaction mixture obtained according to Example 1 and the bromamine-acid sulphate is filtered off at 50°–60° C. and rinsed with 300 ml of 60% strength sulphuric acid. The mother liquor and wash liquor are combined and give 1,094 g of a 72% strength sulphuric acid, which can be reconcentrated by known processes.

Further working up is carried out in accordance with the instructions of Example 1. This gives 233.4 g of the sodium salt of 1-amino-4-bromoanthraquinone-2-sulphonic acid, having the following analysis:
  85.2% of bromamine-acid
  0.5% of 1-aminoanthraquinone-2-sulphonic acid
  0.4% of constituents which have not been sulphonated
  8.2% of water The yield of bromamine-acid is accordingly 80.5% of theory, based on 1-aminoanthraquinone.

EXAMPLE 4

200 g of 1-aminoanthraquinone-2-sulphonic acid (quality 84.8%) are introduced into a mixture of 110 ml of 96% strength sulphuric acid and 145 ml of 20% strength oleum in such a way that the temperature is 65° C. after the acid has been introduced. 0.2 g of iodine is added and the bromination is carried out by adding 21 ml of bromine in portions, at 70°–80° C., in the course of 9 hours. After excess bromine has been removed, in vacuo, 340 g of 30% strength sulphuric acid are allowed to run dropwise into the reaction mixture at 50°–60° C., the mixture is stirred for a further ½ hour and the bromamine-acid sulphate is filtered off and washed with 300 ml of 60% strength sulphuric acid. The mother liquor and wash liquor are combined and give 810 g of a 68% strength sulphuric acid, which can be reconcentrated.

The suction filter cake (604 g) is stirred in 300 ml of water and the mixture is filtered. This gives 390 g of a filtrate containing 32.5% of sulphuric acid, which can be used to dilute a fresh reaction mixture. Since this recycling can be repeated as often as desired, one can remove a total of about 80% of the sulphuric acid employed from the system by reconcentrating and recycling.

The suction filter cake (495 g) is now stirred in 2,000 ml of water, the pH of the suspension is adjusted to 9 with 154 ml of 50% strength sodium hydroxide solution, the suspension is stirred for ¼ hour at 90° C., cooled to 50°–60° C. and filtered and the material on the filter is washed with 1,200 ml of 1.5% strength sodium sulphate solution and dried. This gives 232 g of the sodium salt of bromamine-acid, having the following analysis:
  85.2% of bromamine-acid
  a trace of 1-aminoanthraquinone-2-sulphonic acid
  0.4% of constituents which have not been sulphonated
  8.1% of water The yield of bromamine-acid is accordingly 92.4% of theory, based on 1-amino-anthraquinone-2-sulphonic acid.

EXAMPLE 5

44 g of chlorosulphonic acid are allowed to run dropwise into a mixture of 200 g of 4% strength oleum, 30 g of anhydrous sodium sulphate and 46 g of 97% pure 1-aminoanthraquinone, at 130° C. The mixture is stirred for 3 hours at 130°–135° C. in order to end the sulphonation, then cooled to 80° C. and carefully diluted, at this temperature, with 235 g of 92% strength sulphuric acid. For bromination, 0.1 g of iodine is added and 38 g of bromine are allowed to run in dropwise in portions at 80° C. over the course of 9 hours. For working up, excess bromine is first removed by means of a vacuum and 100 g of water are then allowed to run in dropwise, in order to precipitate the bromamine-acid sulphate. The latter is filtered off and washed with 60% strength sulphuric acid. The suction filter cake is stirred in 600 ml of water, the pH is adjusted to 7 with sodium hydroxide solution and the sodium salt of bromamine-acid is filtered off, washed with 400 g of 1.5% strength sodium sulphate solution and dried. This gives 72.8 g, which are 84.0% pure, in respect to bromamine-acid. This corresponds to a yield of 80% of theory, based on 1-amino-anthraquinone.

EXAMPLE 6

The reaction mixture obtained according to Example 1 by sulphonation and bromination of 1-aminoanthraquinone is stirred into a mixture of 400 ml of 30% strength sulphuric acid and 4 ml of technical grade bisulphite solution, the temperature initially being 60° C. and rising to about 80° C. The mixture is cooled to 40° C. and the product is filtered off and washed with 300 ml of 60% strength sulphuric acid. The mother liquor and wash liquor are combined and give 1,080 g of a 60% strength sulphuric acid, which can be reconcentrated by known processes.

The suction filter cake is worked up in accordance with the instructions of Example 1. This gives 230.4 g of the sodium salt of 1-amino-4-bromoanthraquinone-2-sulphonic acid which is 85.0% pure in respect of bromamine-acid. This corresponds to a yield of 80% of theory, based on 1-aminoanthraquinone.

EXAMPLE 7

20 g of anhydrous sodium sulphate are dissolved in 150 ml of 20% strength oleum and 150 g of 1-aminoanthraquinone are introduced at below 60° C. The reaction mixture is heated at 110° C. for 3 hours, cooled to 80° C. and, after adding 55 ml of 20% strength oleum, heated at 110° C. for a further 3 hours. Subsequently, about 0.1–0.2 g of iodine is added and, at 80° C., 24 ml of bromine are added slowly. After about 16 hours, the bromination is ended by warming the reaction mixture under reflux to 80° C. The excess bromine is removed carefully by applying a vacuum or by blowing out and the sulphate of 1-amino-4-bromoanthraquinone-2-sulphonic acid is precipitated by slow dilution with 135 ml of 30% strength sulphuric acid. The mixture is filtered and the product is washed with 300 ml of 70% strength sulphuric acid and then with 200 ml of 30% strength sulphuric acid. For hydrolysis, the reaction product is stirred in 2,000 ml of water and the pH is adjusted to 1 with 25% strength sodium hydroxide solution at 95° C. A solution then forms. After further addition of sodium hydroxide solution until the pH is 7, the sodium salt of 1-amino-4-bromoanthraquinone-2-sulphonic acid crystallises out. The pH is adjusted to 8-9 with a little sodium carbonate, the mixture is filtered and the product is washed with a dilute solution of sodium sulphate. Yield: 236 g of the sodium salt containing 86.7% of the pure compound.

EXAMPLE 8

150 g of 1-aminoanthraquinone are introduced into 150 ml of 20% strength oleum, with cooling (temperature <60° C.), and the reaction mixture is heated to 110° C. in the course of about 1 hour. This temperature is maintained for about 2 hours, 55 ml of 20% strength oleum are then added slowly at 90° C. and the sulphonation is continued at 110° C. After the reaction has ended (reaction time at least 2 hours), the reaction mixture is brominated and worked up as described under Example 7.

Yield: 226 g of the sodium salt containing 86% of the pure compound.

EXAMPLE 9

The sulphonation is carried out as described in Example 7. For bromination, 0.15 g of iodine and 62.5 g of bromine are added to the reaction mixture and the resulting mixture is heated in a closed reaction vessel for 16 hours at 80° C., while stirring. During this time the pressure rises to 3.5-4 bars. After cooling to 60° C., the reaction vessel is let down to atmospheric pressure, in order to remove carefully excess bromine and hydrogen bromide from the reaction mixture by blowing out or applying a vacuum.

For working up, 108 ml of 70% strength sulphuric acid and then 140 ml of 30% strength sulphuric acid are added slowly, while stirring, 1-amino-4-bromoanthraquinone-2-sulphonic acid precipitating in the form of its sulphate. The mixture is filtered and the product is washed with 375 ml of 70% strength sulphuric acid and with 234 ml of 30% strength sulphuric acid.

The further working up by hydrolysis is carried out as described under Example 7 and, as in that Example, 1-amino-4-bromoanthraquinone-2-sulphonic acid is obtained in equally good quality and yield.

What is claimed is:

1. A process for separating off 1-amino-4-bromoanthraquinone-2-sulphonic acid from the reaction mixture formed by the bromination of 1-aminoanthraquinone-2-sulphonic acid in sulphuric acid, which comprises adjusting the sulphuric acid concentration under the prevailing conditions of temperature and pressure to 60 to 85% by weight of the liquid phase whereby to effect precipitation of 1-amino-4-bromoanthraquinone-2-sulphonic acid as the sulphate and thereafter separating the resultant sulphate precipitate from the reaction mixture.

2. A process according to claim 1 wherein after the precipitate is separated it is contacted with an aqueous solution.

3. A process according to claim 2 wherein said aqueous solution is a solution of an alkali metal hydroxide, alkali metal oxide or alkali metal salt.

4. A process according to claim 1 wherein the sulphuric acid concentration is adjusted to 60 to 85% by weight by adding water which may contain sulphuric acid to the reaction mixture.

5. A process according to claim 1, and 4 wherein the adjustment of the sulphuric acid concentration is performed at a temperature of 50° to 90° C.

6. A process according to claim 1 wherein the reaction mixture is one obtained by sulphonating 1-aminoanthraquinone to obtain 1-aminoanthraquinone-2-sulphonic acid and brominating the resultant reaction mixture to obtain 1-amino-4-bromoanthraquinone-2-sulphonic acid.

7. A process according to claim 2 wherein the precipitate is separated by filtration.

8. A process according to claim 3 wherein a filter cake of said precipitated sulphate is mixed with said aqueous solution of alkali metal hydroxide, alkali metal oxide or alkali metal salt.

* * * * *